US010905335B2

(12) United States Patent
Johnson et al.

(10) Patent No.: US 10,905,335 B2
(45) Date of Patent: Feb. 2, 2021

(54) EMERGENCY MEDICAL SERVICES SMART WATCH

(71) Applicant: ZOLL Medical Corporation, Chelmsford, MA (US)

(72) Inventors: Guy R. Johnson, Gloucester, MA (US); Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 989 days.

(21) Appl. No.: 14/036,313

(22) Filed: Sep. 25, 2013

(65) Prior Publication Data

US 2015/0087919 A1    Mar. 26, 2015

(51) Int. Cl.

| | | |
|---|---|---|
| *A61B 5/0205* | (2006.01) | |
| *A61B 5/00* | (2006.01) | |
| *A61B 5/04* | (2006.01) | |
| *A61H 31/00* | (2006.01) | |
| *A61N 1/39* | (2006.01) | |
| *G16H 20/40* | (2018.01) | |
| *A61B 5/021* | (2006.01) | |
| *G06F 19/00* | (2018.01) | |

(52) U.S. Cl.
CPC ........ *A61B 5/0205* (2013.01); *A61B 5/02108* (2013.01); *A61B 5/04* (2013.01); *A61B 5/486* (2013.01); *A61B 5/4836* (2013.01); *A61B 5/681* (2013.01); *A61B 5/742* (2013.01); *A61B 5/7475* (2013.01); *A61H 31/005* (2013.01); *A61H 31/007* (2013.01); *A61N 1/39044* (2017.08); *G06F 19/3481* (2013.01); *G16H 20/40* (2018.01); *A61B 5/002* (2013.01); *A61B 5/7445* (2013.01); *A61H 2201/0184* (2013.01); *A61H 2201/10* (2013.01); *A61H 2201/501* (2013.01); *A61H 2201/5007* (2013.01); *A61H 2201/5012* (2013.01); *A61H 2201/5046* (2013.01); *A61H 2201/5048* (2013.01); *A61H 2201/5084* (2013.01); *A61H 2201/5097* (2013.01); *A61H 2230/04* (2013.01); *A61H 2230/06* (2013.01); *A61H 2230/207* (2013.01); *A61H 2230/30* (2013.01); *A61N 1/3993* (2013.01)

(58) Field of Classification Search
CPC ......... A61B 5/486; A61B 5/681; A61B 5/742; A61H 31/005; A61H 31/007; A61H 2230/04; A61H 2201/501
USPC ....................................................... 600/301
See application file for complete search history.

(56) References Cited

U.S. PATENT DOCUMENTS

| | | |
|---|---|---|
| 4,589,420 A | 5/1986 | Adams et al. |
| 4,732,158 A | 3/1988 | Sadeh |

(Continued)

FOREIGN PATENT DOCUMENTS

WO   WO93/016636   9/1993

*Primary Examiner* — Nathan J Jenness
(74) *Attorney, Agent, or Firm* — Finch & Maloney PLLC

(57) ABSTRACT

Systems and methods related to the field of cardiac resuscitation, and in particular to devices for assisting rescuers in performing cardio-pulmonary resuscitation (CPR), are described herein. In one aspect, a method for managing cardiopulmonary resuscitation (CPR) treatment to a person in need of emergency assistance includes monitoring a parameter that indicates a fatigue level of a rescuer and providing an indication that a different person should perform the CPR component if the rescuer is exhibiting fatigue.

33 Claims, 8 Drawing Sheets

(56) References Cited

U.S. PATENT DOCUMENTS

| | | | |
|---|---|---|---|
| 4,828,501 A * | 5/1989 | Ingenito | A61B 1/00135 434/262 |
| 4,938,228 A | 7/1990 | Righter et al. | |
| 5,191,891 A | 3/1993 | Righter | |
| 5,333,616 A | 8/1994 | Mills et al. | |
| 5,351,695 A | 10/1994 | Mills et al. | |
| 5,670,944 A | 9/1997 | Myllymaki | |
| 6,238,338 B1 * | 5/2001 | DeLuca | A61B 5/681 128/903 |
| 6,491,647 B1 | 12/2002 | Bridger et al. | |
| 7,272,435 B2 | 9/2007 | Rowlandson | |
| RE40,116 E | 2/2008 | Engstrom | |
| 7,996,187 B2 | 8/2011 | Nanikashvilli et al. | |
| 8,068,900 B2 | 11/2011 | Xue | |
| 2003/0155389 A1 * | 8/2003 | Swartzentruber | A44C 5/12 224/164 |
| 2004/0267325 A1 * | 12/2004 | Geheb | A61B 5/11 607/5 |
| 2007/0060785 A1 * | 3/2007 | Freeman | A61H 31/00 600/16 |
| 2008/0125288 A1 * | 5/2008 | Case | A41D 1/002 482/1 |
| 2008/0171311 A1 * | 7/2008 | Centen | G09B 23/288 434/265 |
| 2010/0056876 A1 * | 3/2010 | Ellis | A61B 5/1038 600/300 |
| 2010/0283616 A1 * | 11/2010 | Ruhs | A61B 5/11 340/573.1 |
| 2011/0117529 A1 * | 5/2011 | Barash | G09B 23/288 434/265 |
| 2011/0288877 A1 | 11/2011 | Ofek et al. | |
| 2012/0092161 A1 | 4/2012 | West | |
| 2012/0123224 A1 * | 5/2012 | Packer | G06F 19/327 600/301 |
| 2013/0131520 A1 * | 5/2013 | Tsubata | A61B 5/0015 600/483 |
| 2014/0081179 A1 | 3/2014 | Moore-Ed | |

\* cited by examiner

EMERGENCY MEDICAL SERVICES SMART WATCH

TECHNICAL FIELD

This document relates to cardiac resuscitation and, in particular, to systems and techniques for assisting rescuers in performing cardio-pulmonary resuscitation (CPR).

BACKGROUND

CPR is a process by which one or more rescuers may provide chest compressions and ventilation to a victim who has suffered an adverse cardiac event—by popular terms, a heart attack. During the first five to eight minutes after CPR efforts begin, chest compressions are considered to be the most important element of CPR because chest compressions help maintain circulation through the body and in the heart itself.

CPR may be performed by a team of one or more rescuers, particularly when the rescuers are professionals, such as emergency medical technicians (EMTs) on an ambulance crew. One rescuer can provide the chest compressions while another can provide and time their ventilations of the victim to match the chest compressions according to the appropriate CPR protocol. When professionals such as EMTs provide the care, ventilation is more likely to be provided via a ventilation bag that a rescuer squeezes rather than by mouth-to-mouth. CPR can be performed in conjunction with shocks to the patient provided by an external defibrillator, such as from an automatic external defibrillator (AED) that is designed to be used by laypeople. Such AEDs often provide audible information to rescuers, such as "push harder" (when the rescuer is not performing chest compressions forcefully enough), "stop CPR," "stand back" (because a shock is about to be delivered), and so on. In order to determine how chest compressions are being performed, certain defibrillators may obtain information from one or more accelerometers (such as in the CPR D PADZ, CPR STAT PADZ, and ONE STEP pads made by ZOLL MEDICAL of Chelmsford, Mass.) that can be used to compute depths of chest compression (e.g., to determine that the compressions are too shallow to be effective and to thus cause the verbal cue "push header" to be spoken by the defibrillator).

SUMMARY

This document describes systems and techniques that may be used to help manage the response to an emergency medical event. Feedback is provided to a rescuer (e.g., a rescuer performing CPR) via a smart watch platform or other wrist-worn device. For example, CPR feedback, such as rate, depth, and CPR interval time, can be displayed on a high pixel density and curved form factor device worn on the rescuer's wrist. Additional feedback, such as release velocity, victim heart rate, inspired carbon dioxide, and/or ventilation prompts, can additionally or alternatively be displayed on the high pixel density and curved form factor device. Other patient information such as ECG or other measured parameters can additionally be displayed. One example of such a high pixel density and curved form factor display is an indium gallium zinc oxide-based display. The wrist-worn device can communicate with a defibrillator or other computing device using a short-range wireless protocol that allows for the combination of high-speed communications and low standby power, such as the Bluetooth 4 protocol.

This document also describes systems and techniques that may be used to help manage the work by teams of rescuers who are responding to a victim or person in need of emergency assistance. For example, typically, such teams include a pair of rescuers, where the first of the rescuers performs CPR chest compressions on the victim and the other performs ventilations, either by mouth-to-mouth techniques or using a flexible ventilator bag. Frequently, a good heartbeat cannot be established quickly for the victim so CPR must be carried out for many minutes in order to maintain perfusion of blood in the victim. In such situations, rescuers can tire after only a minute or two of providing chest compressions, so certain protocols call for the rescuers to switch roles periodically. The systems and techniques discussed here are implemented with recognition that different people have different levels of stamina for performing chest compressions and other components of CPR, such as ventilating a victim or administering drugs to the victim. As a result, the techniques discussed here monitor the physical state of the rescuer, (e.g., by monitoring the heart rate or blood pressure of the rescuer) and tell the rescuers to switch out when the rescuer data indicates that the CPR might be, or would be, better performed by the other rescuer due to tiring of the initial rescuer. This feedback to switch rescuers is provided to a rescuer on a flexible, wrist-worn device, such as a smart watch.

In certain implementations, systems and techniques described herein may provide one or more advantages. For example, a patient may be provided with the best care that is available from the rescue team throughout a rescue episode. For example, a rescuer with greater stamina may be left performing chest compressions longer than another rescuer with less stamina, whereas, alternatively, they might have been allowed to perform for equal time periods, leading to a substandard performance caused by using techniques other than those described here. Also, the terms of each cycle may change as the rescue continues based on the level of physical exertion of the rescuer and the rescuer's physical stamina. Such adjustments may be dynamic and need not rely on a static timed schedule. The instructions to switch may also be provided in a clear and simple manner (and in a variety of manners, such as a visual display worn by the rescuer performing chest compressions), so that even rescuers in a high-stress environment can get the message. In addition, in certain implementations, the techniques described here can be implemented as part of an automatic external defibrillator (AED) or a professional defibrillator, or in a dual-mode defibrillator. As a result, the clinical performance of a rescuing team can be increased, and patient outcomes improved.

In some aspects, a system for managing cardiopulmonary resuscitation (CPR) treatment to a person in need of emergency assistance by a rescuer includes a wrist-worn feedback device configured to be worn on the wrist of a rescuer performing CPR. The wrist-worn feedback device includes a band formed of a material that, upon the application of pressure, wraps around the wrist, securing the wrist-worn device to the rescuer. The wrist-worn feedback device also includes one or more sensors integrated into an inner surface of the band. The one or more sensors are configured to sense one or more parameters that indicate a fatigue level of the rescuer. The wrist-worn feedback device also includes a sensor interface to provide the sensed parameters to one or more external computing devices via a wireless connection, a display formed of a flexible material configured to wrap around the wrist, the display being integrated into an outer surface of the band, and a display interface arranged to receive information about chest compressions from one or more external computing devices and display an indicator on the display based on the received information.

Embodiments can include one or more of the following.

In response to receiving a signal that is based on the fatigue level of the rescuer, the display interface is configured to receive an indication to switch rescuers, and the wrist-worn feedback device is configured to display an indicator on the display based on the received indication to switch rescuers.

The band can be formed of multiple springy metal bands.

The one or more sensors can include sensors configured to monitor the heart rate and blood pressure of the rescuer.

The system can also include an electronic patient monitor, a sensor interface on the patient monitor arranged to receive input from one or more sensors that sense one or more parameters that indicate a quality level of CPR being provided, and a CPR monitor in the electronic patient monitor programmed to use the input from the sensors to identify a quality parameter and to provide information associated with the quality parameter to the wrist-worn device.

The electronic patient monitor can be part of an external patient defibrillator.

The CPR monitor can include a microprocessor connected to electronic memory that stores instructions that, when executed, perform a process of identifying a quality parameter that reflects a depth of chest compressions, rate of compression, or both.

The display can be configured to provide feedback to a rescuer indicating a way to improve the one or more CPR components.

The wrist-worn feedback device can also include a memory configured to store a unique identifier associated with the wrist-worn feedback device.

The wrist-worn feedback device can be configured to turn on when the band wraps around the wrist.

In some additional aspects, a method for managing cardiopulmonary resuscitation (CPR) treatment to a person in need of emergency assistance includes monitoring, with a sensor included in a wrist-worn device, one or more parameters that indicate a status of a user wearing the wrist-worn device, determining, based on the one or more parameters, a fatigue score indicating a level of fatigue of the user of the wrist-worn device, determining, that the fatigue score indicates that the user wearing the wrist-worn device is exhibiting fatigue, and providing a visual indication to the rescuer that a different rescuer should perform the CPR component via a display included in the wrist-worn device.

Embodiments can include one or more of the following.

The method can also include repeating cyclically the actions of monitoring, determining, and providing, while multiple different people are instructed to perform the CPR component.

The CPR component can include chest compressions.

The method can also include receiving one or more parameters that indicate a quality level of a CPR component, the one or more parameters including one or more of depth of compression and rate of compression and determining the fatigue score can include determining the fatigue score based on the one or more parameters that indicate the physical status of the user and the one or more parameters that indicate a quality level of a CPR component.

The method can also include generating a chest compression quality score from a combination of chest compression rate and chest compression depth, and providing an indication of the chest compression quality score to the user via the display included in the wrist-worn device.

The method can also include providing periodic feedback to the user by displaying an indication of values for depths of chest compressions and chest compression rate.

The status can be a physical status.

The method can also include transmitting the fatigue score to a central management system.

In some aspects, a method for managing cardiopulmonary resuscitation (CPR) treatment to a person in need of emergency assistance includes receiving from a sensor included in a wrist-worn device, one or more parameters that indicate a status of a user wearing the wrist-worn device, determining, based on the one or more parameters, a fatigue indicator associated with a level of fatigue of the user of the wrist-worn device, and sending to the wrist-worn device information to cause the wrist-worn device to display a visual indication to the rescuer that a different rescuer should perform the CPR component.

Embodiments can include one or more of the following.

The CPR component can include chest compressions.

The method can also include receiving one or more parameters that indicate a quality level of a CPR component, the one or more parameters including one or more of depth of compression and rate of compression and determining the fatigue indicator can include determining the fatigue indicator based on the one or more parameters that indicate the physical status of the user and the one or more parameters that indicate a quality level of a CPR component.

The method can also include receiving information about the depth and rate of chest compressions, generating a chest compression quality score from a combination of chest compression rate and chest compression depth, and sending to the wrist-worn device information to cause the wrist-worn device to display an indication of the chest compression quality score.

The status can be a physical status.

Other features and advantages will be apparent from the description and drawings, and from the claims.

DETAILED DESCRIPTION

This description discusses systems and techniques for guiding the provision of care to a patient, such as the provision of CPR to a victim of cardiac arrest. For example, a portable electronic defibrillator may be provided to rescuers and may include common features for delivering defibrillating energy (a shock) to a victim of cardiac arrest through electrodes that may be placed on the torso of the victim. The defibrillator may also be provided with a mechanism for sensing the manner in which CPR chest compressions are performed on the victim, such as a puck or similar item that includes an accelerometer, which may be placed under the hands of the person performing chest compressions and on top of the sternum of the victim. The defibrillator may use information from such an item to identify the depth and rate of chest compressions that are being performed by a rescuer. Feedback can be provided to the rescuer via a curved form factor display worn on the wrist of the rescuer such as a smart watch with an indium gallium zinc oxide high pixel density display.

In some embodiments, the wrist-worn device can include one or more sensors to track the physiological state of the rescuer by monitoring factors of the rescuer such as pulse and blood oxygen level. This information can be used to assess the fatigue level of the rescuer and make a determination as to when multiple rescuers at the scene of the rescue event should switch performing CPR. When the defibrillator makes a determination that the rescuer is suffering from fatigue, the defibrillator may provide an indication to that rescuer that he or she should step away and allow another rescuer to perform chest compressions for a time. Such an indication can be provided through the smart watch worn by the rescuer. For example, where there are two rescuers, the second rescuer may have been providing ventilation to the victim using a ventilation bag and may be simultaneously prompted to change and provide chest compressions, while the first rescuer takes over operation of the bag.

Figure 1:
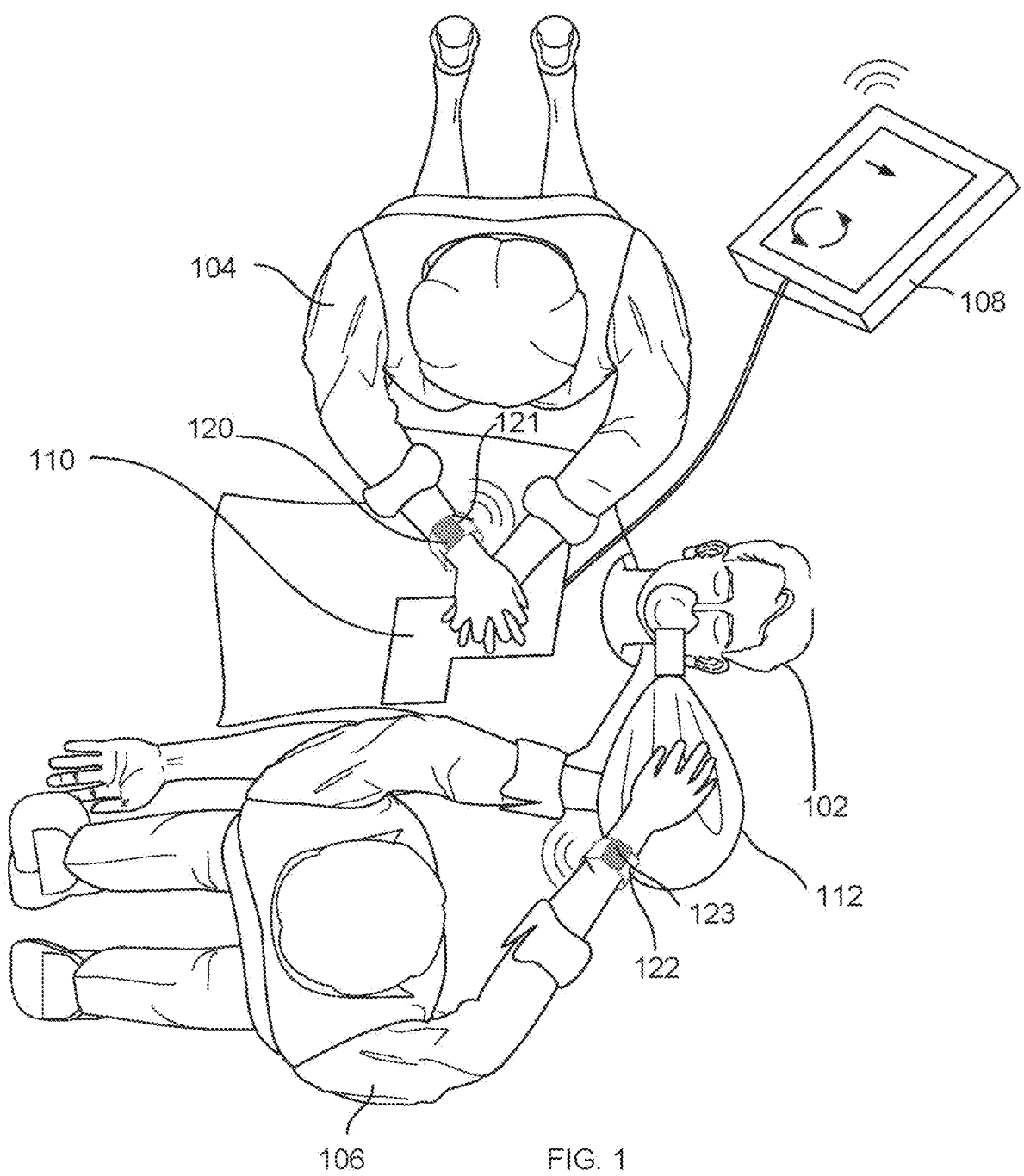
FIG. 1 is an overhead view of rescuers performing CPR on a victim using an electronic system that instructs them in their performance of the CPR.

FIG. 1 is an overhead view of rescuers 104, 106 performing CPR on a victim 102 using an electronic system that instructs them in their performance of the CPR. Each of the rescuers 104, 106 wears a wrist-worn device 120, 122, such as a smart watch, with a curved form factor display 121, 123. The wrist-worn devices 120, 122 provide feedback to the rescuers performing the CPR on the victim 102.

In this example, rescuers 104, 106 are already in position and providing care to the victim 102, with rescuer 104 and providing chest compressions to the torso of the victim 102, and rescuer 106 providing ventilation using ventilation bag 112. The rescuers 104, 106 may be lay rescuers who were in the vicinity of the victim 102 when the victim 102 required care, or may be trained medical personnel, such as emergency medical technicians (EMTs). Although two rescuers are shown here for purposes of explanation, additional rescuers may also care for the victim 102.

Control and coordination for the resuscitation event and the delivery of the various therapies may be accomplished by a device or processing element that is external to the defibrillator 108, such as by use of a tablet-based computer that is controlled by one of the rescuers. For instance, the device may download and process ECG data from the defibrillator 108, analyze the ECG signals, perform relevant determinations based on the analysis, and control the other therapeutic devices. In other examples, the defibrillator 108 may perform all the processing of the ECG, including analyzing the ECG signals, and may transmit only the final determination of the appropriate therapy to a separate device, whereupon the separate device can perform the control actions on the other linked devices.

An electrode assembly 110 is shown on the victim 102 in a normal position. The electrode assembly 110, in this example, is an assembly that combines an electrode positioned high on the right side of the victim's torso, a separate electrode positioned low on the left side of the victim's torso, and a sensor package located over the victim's sternum. The sensor package, which, in this example, is obscured in the figure by the hands of rescuer 104 may include an accelerometer or similar sensor package that may be used in cooperation with a computer in the defibrillator 108 to monitor performance of the chest compressions.

The defibrillator 108 in this example is connected to the electrode package 110 and may operate in a familiar manner (e.g., to provide defibrillating shocks to the electrode package 110). As such, the defibrillator may take a generally common form, and may be a professional style defibrillator, such as the R-SERIES, M-SERIES, or E-SERIES from ZOLL Medical Corporation of Chelmsford, Mass., or an automated external defibrillator (AED), including the AED PLUS, or AED PRO from ZOLL Medical Corporation.

The defibrillator or a computing device associated with the defibrillator communicates wirelessly with the wrist-worn devices 120, 122 to present information to the rescuers. For example, information can be visually presented on the displays 121, 123. Additionally, vibrators or audible sound generators on the wrist-worn devices 120, 122 can provide feedback. Such feedback, as discussed more fully below, may include information about physical status of the victim 102 and performance of CPR.

The wrist-worn devices 120, 122 can be smart watches (e.g., computerized wristwatches with functionality enhanced beyond timekeeping). Such a smart watch can effectively be a wearable computer. The smart watch can include a data processor, memory, input and output. The smart watch collects information from internal sensors. It may control or retrieve data from other instruments or computers. For example, the smart watch can support wireless technologies, like Bluetooth and/or Wi-Fi, to communicate with the defibrillator 108 or another computing device. In other examples, the smart watch may just serve as a front end for a remote system and be configured to display information generated by the defibrillator or associated computing device. The displays 121, 123 in the wrist-worn devices 120, 122 can be made of Indium gallium zinc oxide (IGZO), a semiconducting material. IGZO thin-film transistors (TFT) can be used in the TFT backplane of flat-panel displays (FPDs). Because the IGZO display is flexible, a greater amount of information can be displayed on the wrist-worn devices 120, 122 due to the increased surface area of the display.

Figure 2A:
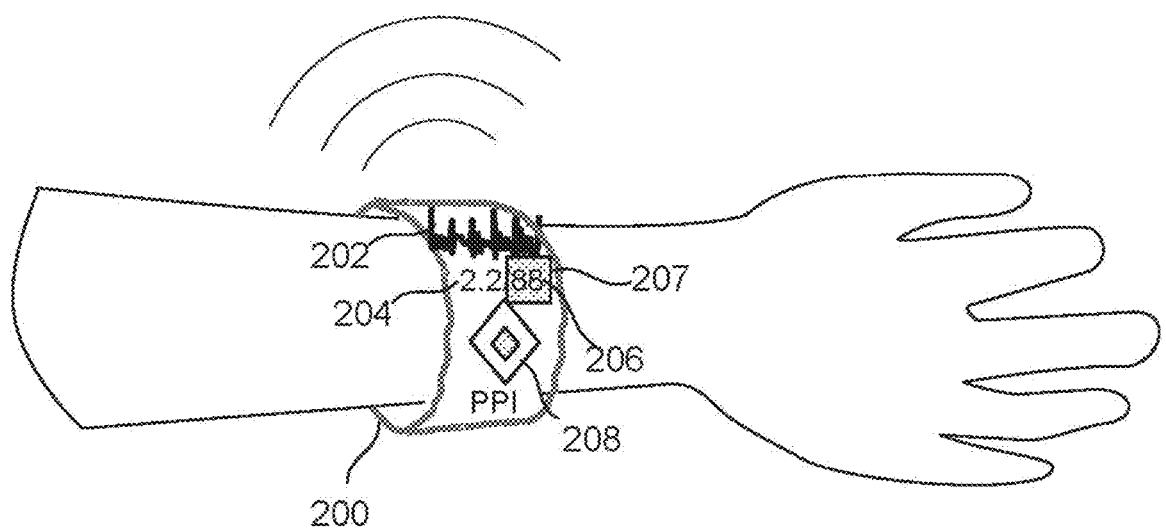
FIGS. 2A and 2B show exemplary smart watches displaying information associated with a rescue attempt.
Figure 2B:
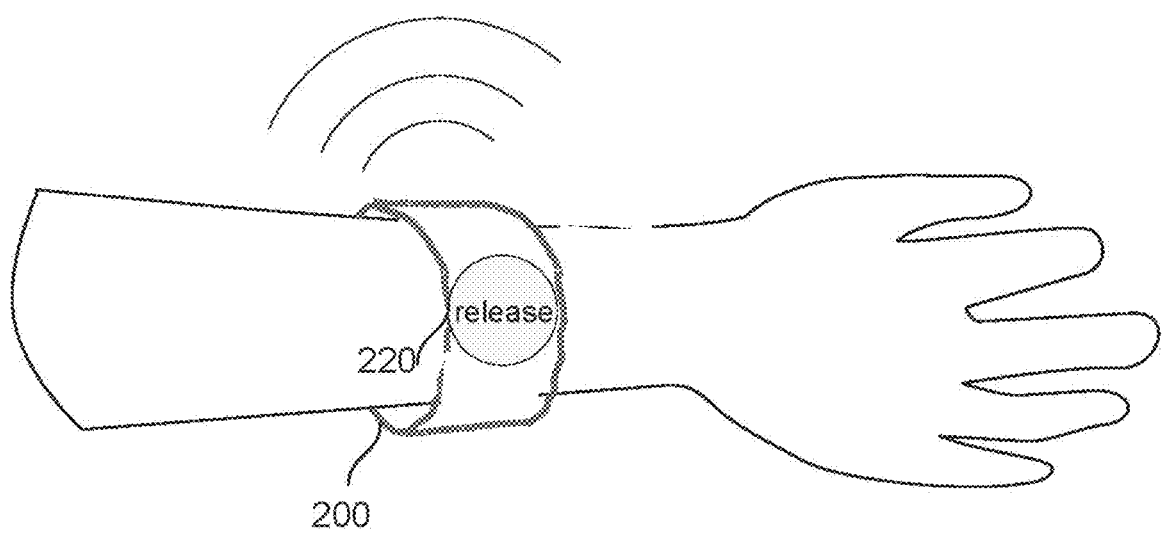

For illustrative purposes, two particular examples of feedback provided to a rescuer on the display of the wrist-worn devices are shown in FIGS. 2A and 2B.

As shown in FIG. 2A, a wrist-worn device 200 provides information about the physiological state of the patient, as well as information about the quality of the CPR being performed by the rescuer. The display includes CPR information that is automatically displayed when compressions are detected by a defibrillator. The displayed information about the chest compressions includes rate 206 (e.g., number of compressions per minute) and depth 204 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can provide useful feedback to the rescuer. A visual indicator 207, such as a color of the text or an applied highlighting, can be modified to indicate when a value for the depth or rate is outside of the preferred range. The displayed information about the chest compressions also includes a perfusion performance indicator (PPI) 208. The PPI 208 is a shape (e.g., a diamond) with the amount of the shape that is colored or shaded (e.g., the fill amount) differing over time to provide feedback about both the rate and depth of the compressions. When CPR is being performed adequately, the entire indicator will be filled. As the rate and/or depth decreases below acceptable limits, the amount of fill lessens. The PPI 208 provides a concise visual indication of the quality of the CPR such that the rescuer can aim to keep the PPI 208 completely filled.

As shown, the display on wrist-worn device 200, a filtered ECG waveform 202 can fill the entire span of the display device. In some additional examples, a second waveform (e.g., the CO2 waveform) is additionally provided on the display.

The data displayed to the rescuer can change based on the rescuer's actions. For example, the data displayed can change based on whether or not the rescuer is currently administering CPR chest compressions to the patient. In another example, if multiple rescuers are present, this CPR information can be displayed to only the rescuer who is performing the CPR and other information, such as the patient data and/or ventilation feedback, can be provided to the other rescuers.

As shown in FIG. 2B, the display on wrist-worn device 200 can additionally or alternatively provide concise, simplified feedback with instructions to the rescuer regarding how to perform CPR. In this particular example, the display provides a reminder 220 regarding "release" in performing chest compression. Specifically, a fatigued rescuer may begin leaning forward on the chest of a victim and not release pressure on the sternum of the victim at the top of each compression. This can reduce the perfusion and circulation accomplished by the chest compressions. The reminder 220 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. For example, the visual indication may be accompanied by vibration generated by the wrist-worn device 200 in order to indicate that a rescuer is to stop and modify how they are performing the CPR. For example, the wrist-worn device may be provided with mechanisms for vibrating the device similar to mechanisms provided for vibrating portable communication devices (e.g., when an incoming telephone call is received on a smartphone). Such vibrating may be provided so as to alert the user to particular information and/or minimize the amount of information that can distract other rescuers in the area.

In another example, the wrist-worn device 200 can generate periodic vibrations felt by the user to synchronize his/her chest compression activities with the output. For example, the vibrations may be periodic occurring at the preferred chest compression rate (approximate 100 times per minute) to indicate when the rescuer 104 should be performing compressions. Such haptic feedback, when used to identify urgent information or provide instructions, may also relieve the rescuer 104 of having to constantly monitor the display on the wrist-worn device 200. Thus, a first type of feedback, which may be pulsed visual, audible, or tactile, may be provided to signal the wearer of the wrist-worn device 200 of a need to view information displayed on the display.

Figure 3:
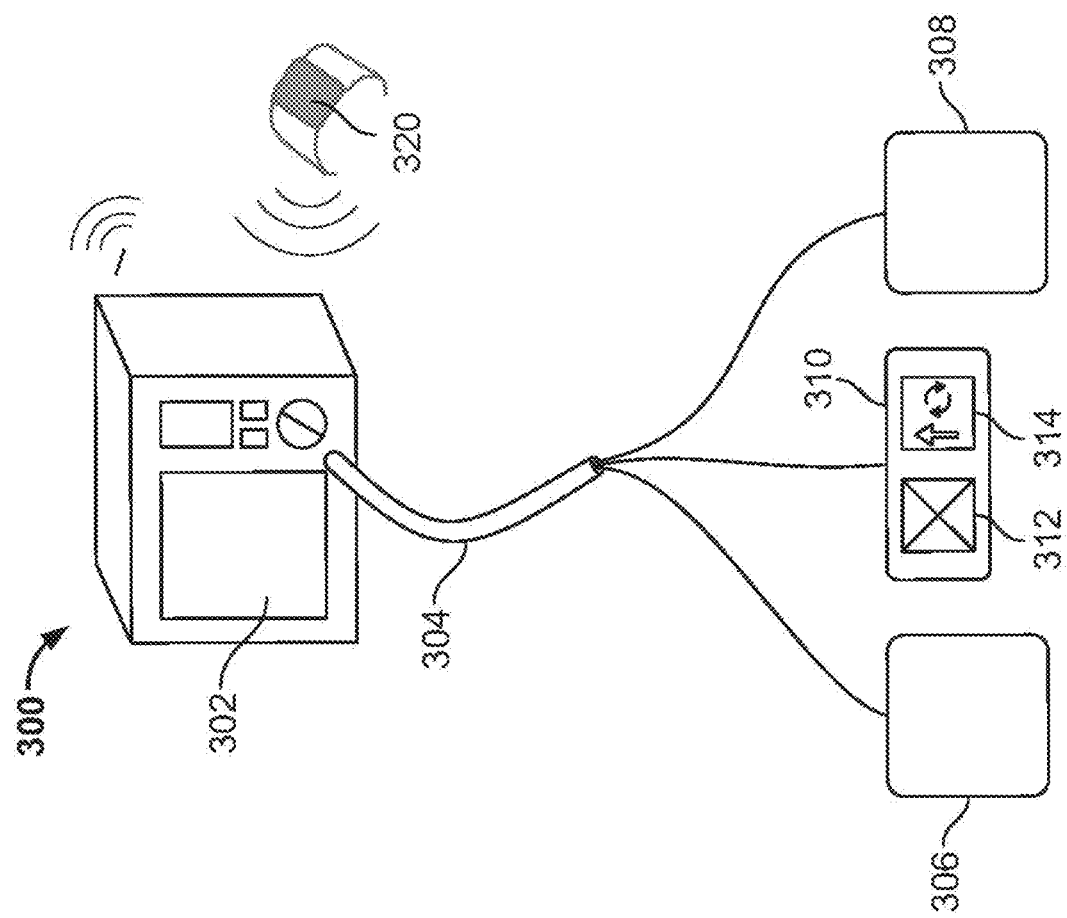
FIG. 3 shows a portable defibrillator and ancillary components arranged to provide feedback and instruction to rescuers.

FIG. 3 shows a portable defibrillator 302 and ancillary components arranged to provide feedback and instruction to rescuers via a smart watch 320. The smart watch 320 provides a display on which visual feedback can be provided to a rescuer at a location that is away from the defibrillator unit 302, and more immediately in the line of sight and focus of attention of a rescuer.

In system 300, the defibrillator 302 is connected to an electrode assembly by way of a wiring harness 304. The wiring harness 304 may include a number of wire leads and may be connected to the defibrillator 302 by way of a single plug. The wires may carry power from the defibrillator 302, such as current to provide a shock to a victim who is being provided with emergency care, or to the defibrillator 302, such as in the form of signals for generating ECG information, accelerometer information, and measurements of transthoracic impedance of a victim. The electrode assembly in this example includes a first electrode 306, a second electrode 308, and a chest compression assembly 310. The first electrode 306 may be configured to be placed above the victim's right breast, while the second electrode 308 may be configured to be placed below the victim's left breast. The chest compression assembly 310, in this example, includes a detector 312 and a display 314. The detector 312 may include a plastic housing within which an accelerometer assembly is mounted. The accelerometer assembly may move with the housing as chest compressions are performed on a victim so that motion of the accelerometer matches motion of the victim's sternum. The accelerometer in the housing may be connected to defibrillator 302 in order to pass signals through harness 304 (or may include a wireless transceiver for passing the information wirelessly). The defibrillator 302 may be provided with circuitry and/or software for converting such signals into the indications regarding the rate and depth of compressions being performed on the victim, in manners such as those described below. The display 314 may provide feedback that is directed to the rescuer who is performing chest compressions. In this example, the feedback can include similar feedback that is provided to the rescuer via the smart watch 320. For example, the display 314 can show feedback about CPR performance such as, an arrow indicating when the user is to perform chest compressions more vigorously and circular cycling arrows indicating when rescuers are to switch in performing chest compressions. In some examples, the accelerometer can be included in the watch 320.

The defibrillator 302 communicates with the smart watch 320 via a wireless connection. For example, the defibrillator 302 can communicate with the smart watch 320 using a wireless technology standard for exchanging data over short distances, such as Bluetooth technology, which uses short-wavelength radio transmissions in the ISM band from 2400-2480 MHz to form personal area networks (PANs) with high levels of security. Thus, the defibrillator 302 and the smart watch 320 each include a transmitter and a receiver for sending and receiving the wireless communications.

Figure 4:
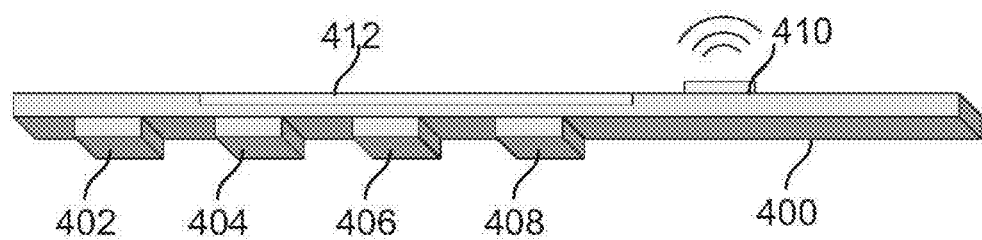
FIG. 4 shows an exemplary device including a display, sensors, and a communication module configured to be worn on the wrist of a rescuer.

FIG. 4 shows an exemplary smart watch 400 used to capture information from a rescuer and provide feedback to the rescuer via a display 412. One or more sensors can be used to capture information about the rescuer. When the rescuer places the smart watch 400 on his or her wrist, the one or more sensors are placed in contact with the rescuer's skin such that information about the physical state of the rescuer can be monitored. For example, the smart watch 400 can include a blood pressure sensor 402, a pulse oximetry sensor 404, and a colorimeter 408. In general, the pulse oximetry sensor 404 can be used to provide a (wirelessly) connected medical device, such as a defibrillator, with indications of the blood oxygen level and pulse rate of a rescuer wearing the device. In general, the blood pressure sensor can be used to provide a connected medical device, such as the defibrillator, with indications of the blood pressure of the rescuer. The colorimeter 408 is configured to obtain a spectra based on an intensity of light reflected primarily from the epidermis and dermal papillae of an individual's skin. The colorimeter 408 may take the form of a spectrophotometer, which generates spectral reflectance/absorbance data and provides a quantitative measurement of the reflection or absorption properties of a material as a function of wavelength. An exemplary colorimeter 408 is described in U.S. patent application No. 61/836,803, filed on Jun. 19, 2013 and titled "Analysis of skin coloration," the contents of which are hereby incorporated by reference in its entirety.

The smart watch 400 also includes a wireless transmitter/receiver 410. Information collected by the blood pressure sensor 402, pulse oximetry sensor 404, and colorimeter 408 can be sent to a remote processing device, such as a remotely located computing device or a computing device in a defibrillator via the wireless transmitter/receiver 410. Additionally, the smart watch 400 can receive information from the remotely located computing device or the computing device in the defibrillator via the wireless transmitter/receiver 410. The information received by the wireless transmitter/receiver 410 can be used to provide feedback to the rescuer about his/her performance during the rescue event. For example, the smart watch 400 can receive information to cause a display device 412 in the smart watch 400 to display information and feedback to the rescuer, such as the information and feedback described herein. Additionally, the smart watch 400 can receive commands to cause a tactile feedback device, such as a buzzer or vibration device 406, to provide additional stimulus to the user.

During use, the smart watch 400 is affixed around a user's wrist. The entire watch (including display 412) is flexible such that the display forms a curved surface and the various sensors located on the underside of the device will contact the rescuer's skin. In some examples, the smart watch 400 can include a band that is formed of layered, flexible stainless steel bi-stable spring bands sealed within a fabric or plastic cover. The display 412 is incorporated into a top surface of the band and the sensors 402, 404 and 408 are incorporated into a bottom or opposite surface of the band. The band can be straightened out, causing tension within the springy metal bands. The straightened bracelet is then slapped against the wearer's forearm, causing the bands to spring back into a curve that wraps around the wrist, securing the band to the wearer. Thus, no buckles or other fastening devices are required to secure the smart watch 400 to the rescuer's wrist. Rather, an applied force or pressure causes the band of the device to assume a shape that secures itself to the rescuers wrist. In some examples, the smart watch 400 can include a sensor or unit configured to sense when the smart watch 400 is secured to the rescuer's wrist (e.g., sense when the shape of the watch changes from being straight to being curved). The unit causes the smart watch 400 to turn on (e.g., apply power to the unit) upon sensing that the smart watch 400 has been secured to the rescuer's wrist. Thus, the wearer does not need to take additional actions to turn-on the smart watch 400 because the smart watch 400 turns on automatically upon modification of the shape of the band.

As described above, the smart watch device can include sensors that monitor the rescuer. Such values may then be used either independently or along with other factors, such as rate and depth of compressions, to determine when the rescuer should be instructed to stop performing chest compressions and yield to another rescuer. Also, the feedback provided to the rescuer on the smart watch can integrate information about rescuer blood oxygen level, pulse, or both in order to determine the feedback to be provided to the rescuer. Thus, for example, a processor may receive signals from the sensors and convert them partially or fully into blood oxygen and pulse rate values that can then be displayed or further processed (e.g., to identify that the rescuer is becoming fatigued).

Figure 5:
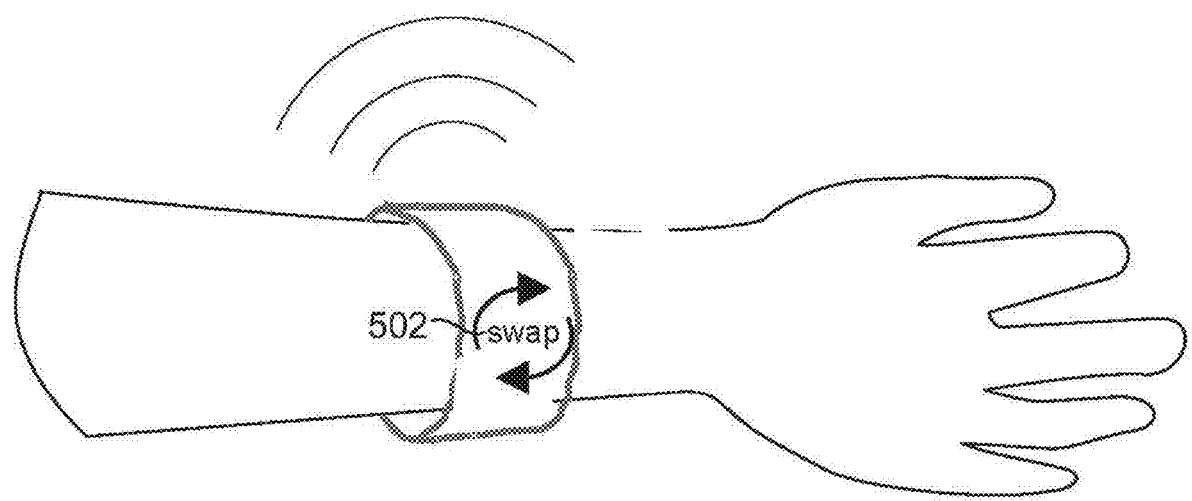
FIG. 5 shows an exemplary smart watch displaying an indication that the provider of care should change.

In one example, as shown in FIG. 5, feedback can be provided using a visual indicator on the smart watch indicating that the rescuer should change places with another rescuer. In this example, cycling arrows 502 are displayed on the smart watch display screen. Such arrows may indicate to the rescuers that it is time for them to switch tasks. Using the example shown in FIG. 1, providing a rescuer swap indicator can indicate that that rescuer 104 should cease providing chest compressions and begin operating the ventilation bag 112 and rescuer 106 should cease controlling the ventilation and instead began providing chest compressions on electrode assembly 110. When there are three or more rescuers, the third rescuer may have been resting and can take over chest compressions for rescuer 104 when a rescuer change is directed by the system. The rescuer 104 may then rest or switch from providing chest compressions to providing ventilation assistance while rescuer 106 rests or does something else. The defibrillator may cause the cycling arrows 502 to be displayed based on the occurrence of various events. In one example, the cycling arrows 502 may be displayed after a set time period has elapsed since rescuer 104 began applying chest compressions. A particular CPR protocol may require switching of rescuers at certain predefined periodic intervals (e.g., every 2 minutes). As described previously as well as below in more detail, the cycling arrows 502 or a similar cycling signal, may alternatively be generated according to determinations made by the defibrillator regarding the level of rescuer fatigue. The defibrillator may thus be programmed to identify when factors indicate the rescuer's physical state (e.g., via pulse measurement) has started to decline. For example, a heart rate monitor in the smart watch can measure an increase in heart rate that may indicate fatigue by the rescuer and may be used to generate a signal to switch rescuers. A rescuer fatigue score can be calculated and compared to a threshold such that when the rescuer fatigue score exceeds the threshold, the system indicates that the rescuer should allow someone else to take over, by displaying cycling arrows 502, for example. In another example the system combines information about the length of time the rescuer has performed CPR with the rescuer fatigue information to determine a rescuer fatigue score.

Figure 6:
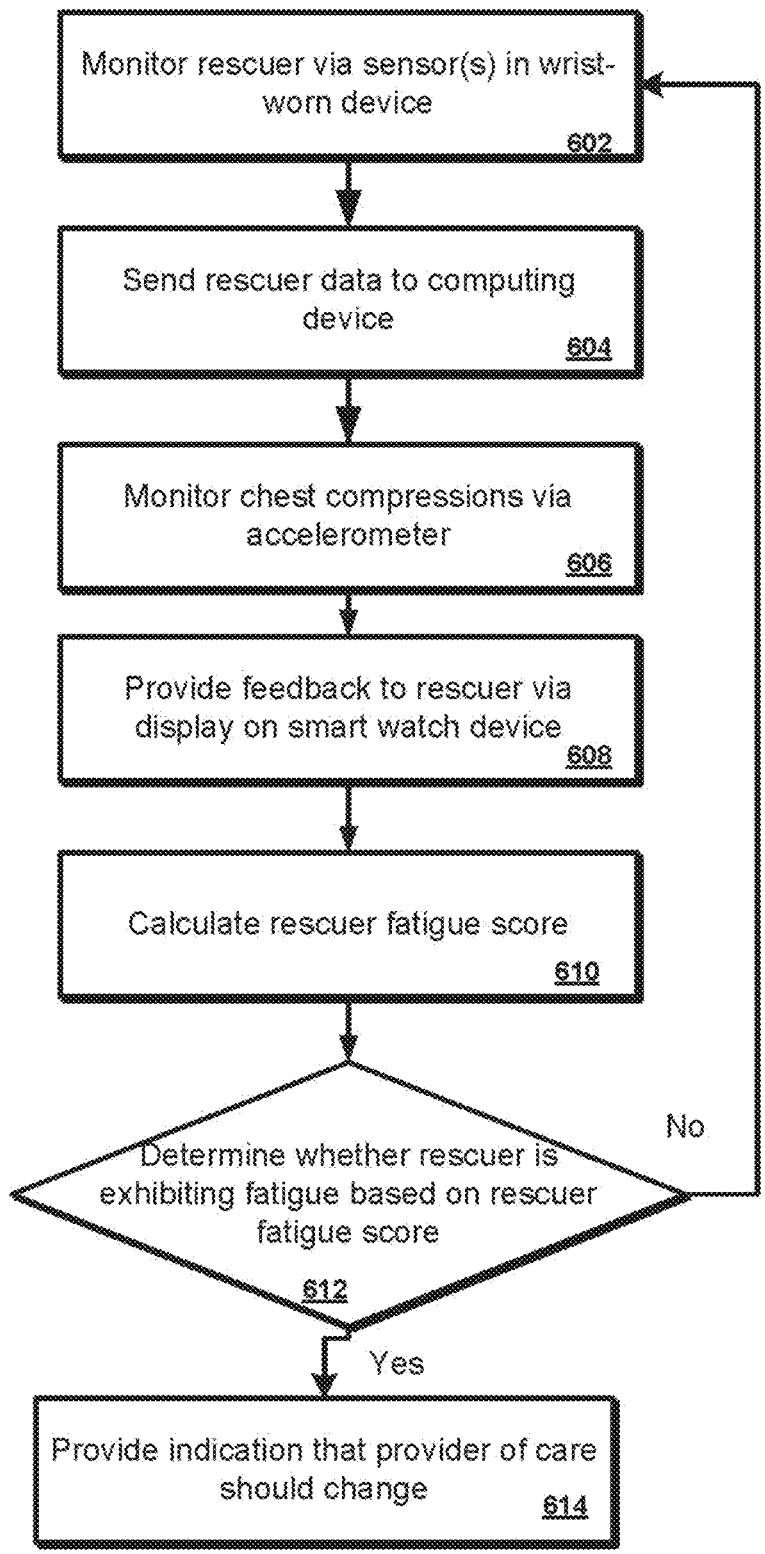
FIG. 6 is a flowchart of a process for monitoring rescuer status and providing an indication of when the provider of care should change.

FIG. 6 is a flowchart of a process for monitoring CPR performance and a rescuers physical state and providing feedback for improvement of the performance. Generally, the process involves automatic monitoring of the performance of a component of CPR, such as the provision of chest compressions to a victim, and providing an indication of when the provider/rescuer should stop performing the component and allow another rescuer to take over.

The process begins at box 602, where it monitors the physical state of the rescuer using various sensors included in a wrist-worn device. For example, the process can receive data indicative of one or more of the patient's blood pressure, heart rate, and inspired CO2. At box 604, this data is sent to a computing device. For example, the data can be sent from the wrist-worn device to a computing device in a defibrillator using a wireless protocol.

At box 606, the process monitors chest compressions via an accelerometer puck. For example, the rescuer may have applied the electrodes and the puck and have begun performing chest compressions on the victim. Such compressions may cause the puck to move and accelerate up and down, so that an accelerometer in the puck generates signals indicative of such acceleration. The defibrillator may receive such signals and convert them into indications of the quality of the chest compression, such as indications of how deep each chest compression is and the pace at which particular ones of the chest compressions are occurring.

At box 608, the process generates feedback related to the rescuer's performance of CPR and provides the feedback to the rescuer on a display of the smart watch device. This information can include the depth and rate of chest compressions. Additionally, the feedback provided to the rescuer can include information about the patient status, such as a display of the ECG or SpO2 signaled.

At box 610, the process calculates a fatigue score based on the received rescuer monitoring data alone or in combination with the observed prior chest compressions. For example, the fatigue score may be computed as a function of the measured physical status of the rescuer. In another example the fatigue score may be computed as a function of the measured physical status of the rescuer in combination with the depth and rate of one or more chest compressions that have been observed from the accelerometer puck.

At box 612, a determination is made with regard to whether or not the fatigue score indicates a need to change the roles of the rescuers. For example, if a fatigue score is below a threshold that indicates an acceptable level of fatigue, the process returns back to box 602 and continues monitoring a rescuers physical status and the chest compressions using the accelerometer puck as well as determining the fatigue scores.

If the fatigue score exceeds the threshold indicating that the rescuer has begun to fatigue, at box 614, the process provides an indication to the rescuer, and perhaps to others, that a provider of care should change. For example, the smart watch can provide a visual indication that the provider of care should change. In addition, haptic feedback may be provided to the rescuer, such as switching from periodic (metronomic) vibration in a unit in the wrist-worn device to continuous vibration in the wrist-worn device, or another change in haptic feedback that differs from the feedback given when no change is to be made.

Using such a process, a system may then adjust to the capabilities of various caregivers and maintain caregivers in a position to provide a particular component of care as long as they are able to provide for it. As a result, the system need not be stuck to preset time limits that might not reflect the actual standard of care that can be adequately provided, but can instead vary based on the actual standard of care that is being given by a particular rescuer team in a particular situation. The process could result in better outcomes for victims tended to by such rescuers, and in a better experience for the rescuers themselves.

Figure 7:
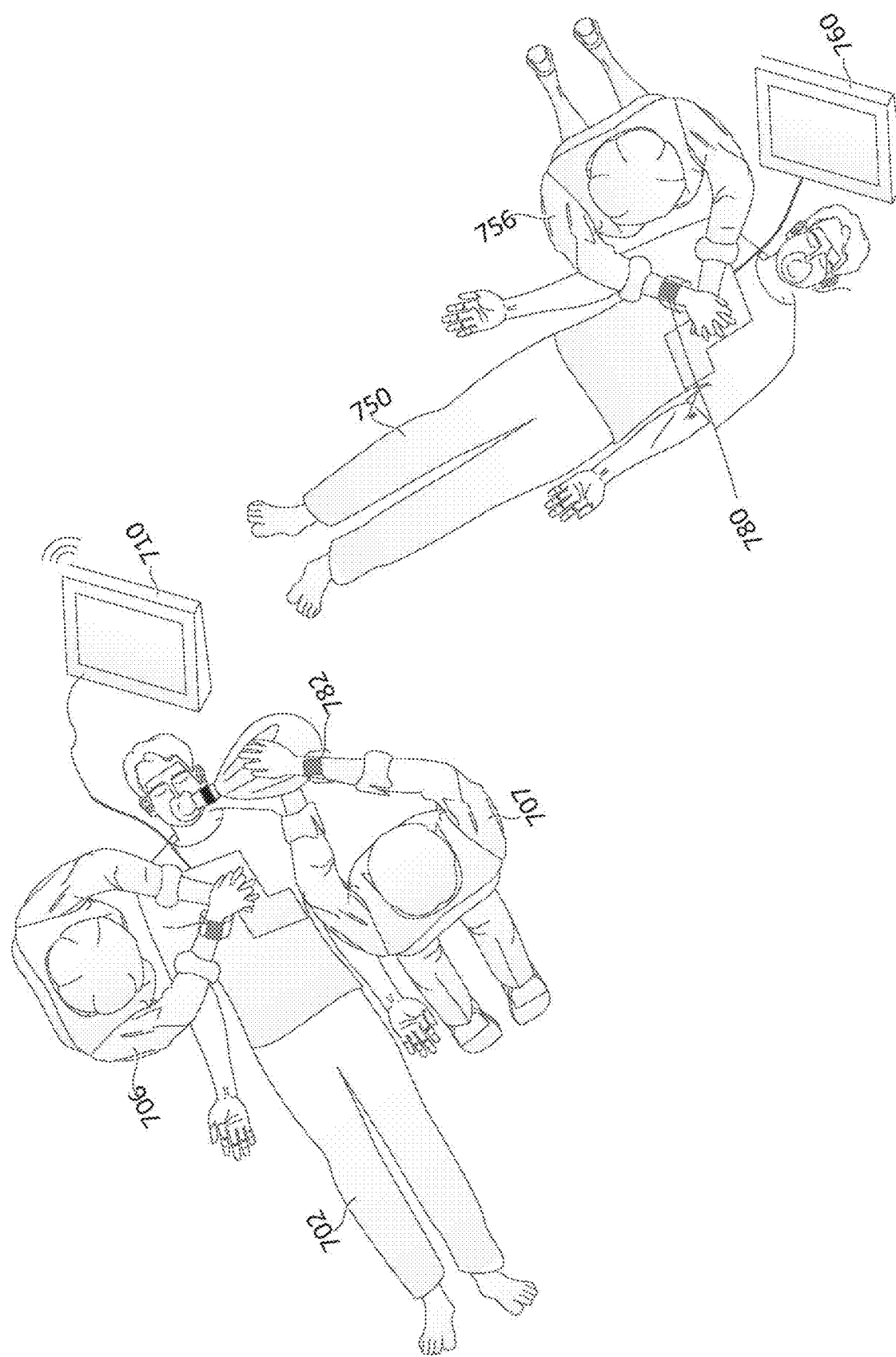
FIG. 7 is an overhead view of rescuers performing CPR on a victim using an electronic system that instructs them in their performance of the CPR.

In systems where smart watches communicate wirelessly with a central computing device, such as the defibrillator, it is important to ensure that the smart watches are paired with the correct central computing device. For example, as shown in FIG. 7, at the scene of a mass casualty or mass rescue event, there can be multiple different patients 702, 750. It is essential that the smart watches for a particular patient are correctly paired with the computing device or defibrillator associated with that patient. For example, the smart watches 784 and 782 should be wirelessly connected with the central computing element in defibrillator 710 while the smart watch 780 should be wirelessly connected to the central computing element in defibrillator 760. If, for example, the smart watches 784 and 782 associated with patient 702 were instead mistakenly wirelessly connected to defibrillator 760. The information displayed to the wearers would not be accurate. Additionally, the decisions of if/when to switch rescuers might be incorrect. In an extreme case, if patient 702 regained blood circulation and breathing and the sensors were mistakenly connected to the defibrillator 760, defibrillator 760 could erroneously instruct the rescuer 756 to discontinue administration of CPR on victim 750. In another example, if ECG information were erroneously transmitted to an incorrectly matched defibrillator, the defibrillator could erroneously shock a victim whose heart rhythm was non-shockable. In order to prevent such detrimental situations, it is important to ensure that the sensors are paired with the correct central computing device.

Correct pairing of a smart watch with the patient-specific, localized network occurs when the smart watch is connected to the wireless network. Smart watches (and thereby the rescuers) can join and leave various networks so that they can aid in different rescue attempts. For example, as rescuer 756 begins to fatigue, rescuer 706 might leave the rescue attempt for victim 702 and join the rescue attempt for victim 750. In doing so, the information displayed on the smart watch 782 worn by rescuer 706 should be changed to display the data for victim 750.

Various mechanisms can be used to allow a rescuer (and their smart watch) to join/leave a particular network. For example, the smart watch can have a touch menu allowing the user to select a particular network from a list of networks. In another example, the smart watch can include mechanisms that allow a particular network to be selected based on actions of the user/watch without requiring the user to know and select the network. For example, a bump-to-join process could be executed in which, upon two smart watches contacting one another, the second smart watch joins the network of the first.

Figure 8:
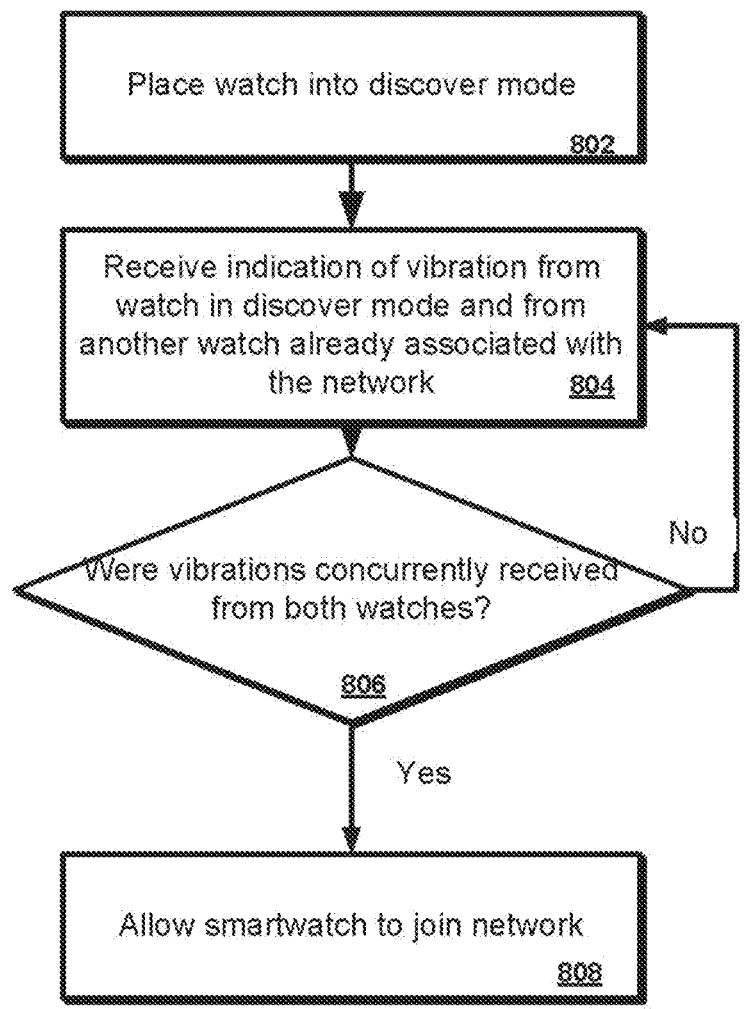
FIG. 8 is a flowchart of a process for joining a network.

FIG. 8 shows a process for adding a smart watch to a network associated with a particular defibrillator/patient. The process begins with a wearer of a smart watch desiring to join a particular network associated with a rescue attempt. The wearer places the smart watch into a discover mode (802). In the discover mode, the smart watch is granted/denied access to the network based on the concurrent receipt of signals from multiple smart watches. The concurrently received signals are indicative of the wearer's association with a particular rescue team. For example, in the scene of a mass rescue attempt where multiple different networks exist, the rescuer is connected to the correct network associated with the victim they will aid (e.g., as described in relation to FIG. 7) based on the concurrently received signals. The defibrillator or central computing device receives an indication of vibration from the watch in discover mode and from another watch already associated with the network (804). For example, each of the smart watches can include an accelerometer and the two wearers can shake hands or give a high five such that the accelerometers in each of the watches will concurrently measure a motion. The defibrillator or central computing device determines whether the vibrations were concurrently received from both watches (806). If the measured vibrations were concurrent, the system allows the smart watch in discovery mode to join the wireless network of the watch already associated with the network (808). Thus, a particular network is selected from amongst multiple different networks based on the network associated with the watch for which the concurrent signal was received. If the measured vibrations were not concurrent, the system returns to receiving vibration indications from the watch.

In some examples, a central management system can be connected to one or more smart watches and to other computing devices and the defibrillator associated with a patient rescue. As such, the central management unit can gather information about the rescue attempt and information about the rescuer performance.

Figure 9:
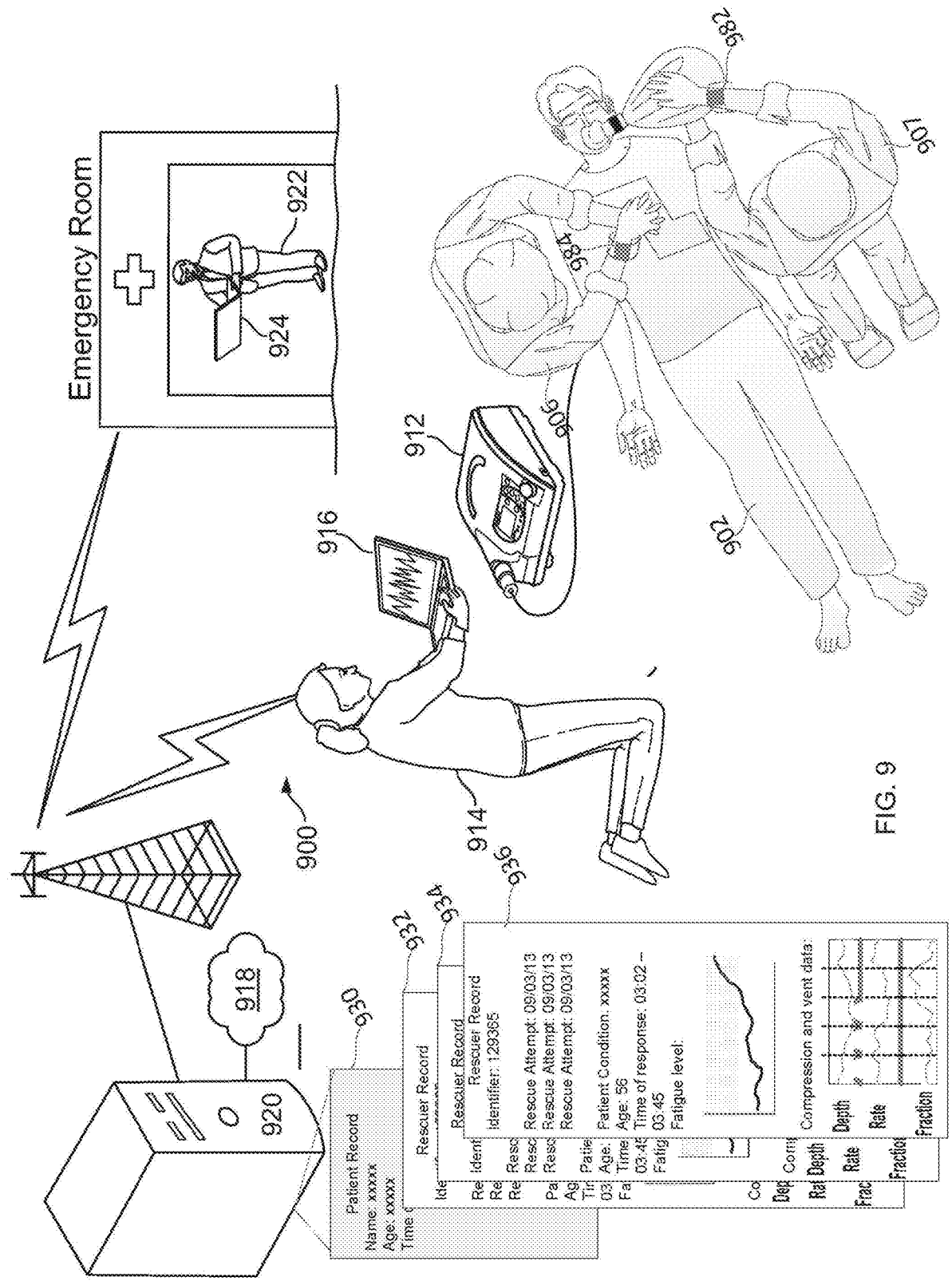
FIG. 9 is an overhead view of rescuers performing CPR on a victim using an electronic system that instructs them in their performance of the CPR.

In one particular example, FIG. 9 shows a system 900 for responding to an emergency medical condition of a victim 902. In general, system 900 includes various portable devices for monitoring on-site care given to the victim 902. The various devices may be provided by emergency medical technicians who arrive at the scene and who provide care for the victim 702, such as emergency medical technicians 906, 907 and 914. In this example, the emergency medical technician technicians 906, 907 and 914 have deployed several devices and are providing care to the victim 902. The emergency medical technician 914 in this example is interacting with a computing device in the form of a touchscreen tablet 916. The tablet 916 may include a graphical display by which to report information to the emergency medical technician 914. A portable defibrillator 912 is shown in a deployed state and is connected to the victim 902. In addition to providing defibrillation, the defibrillator 912 may serve as a patient monitor via a variety of sensors or sensor packages. For example, as shown here, electrodes have been applied to the bare chest of the victim 902 and have been connected to the defibrillator 912, so that electrical shocking pulses may be provided to the electrodes in an effort to defibrillate the victim 902, and electrocardiogram (ECG) signals may be read from the victim 902. The defibrillator 912 may provide feedback in a conventional and known manner to a rescuer, such as emergency medical technician 914.

The defibrillator 912 may communicate through a short range wireless data connection with the tablet 916. The defibrillator 912 can provide to the tablet 916 status information, such as information received through the electrode assembly, including ECG information for the victim 902. Also, the defibrillator 912 can send information about the performance of chest compressions, such as depth and rate information for the chest compressions. The tablet 916 can also receive data from the other sensors associated with the victim 902 such as an airflow sensor provided with a ventilation bag. The tablet 916 can also receive data from smart watches 984 and 982 worn by rescuers 906 and 907 respectively. The information from smart watches 984 and 982 can include information about the fatigue level of the rescuer (e.g., as described herein).

A central server system 920 may communicate with the tablet 916 or other devices at the rescue scene over a wireless network and a network 918, which may include portions of the Internet (where data may be appropriately encrypted to protect privacy). The central server system 920 may be part of a larger system for a healthcare organization in which medical records 932 are kept for various patients in the system. Information about the patient 902 may then be associated with an identification number or other identifier, and stored by the central server system 920 for later access. Additionally, the central server system 920 may store records 932, 934, 936 that include information associated with each of the rescuers for various rescuers in the system. Information about the each of the rescuers may then be associated with an identification number or other identifier, and stored by the central server system 920 for later access. This information can include each rescue attempt in which the rescuer participated and their role in the rescue. Additionally, the information about the rescuer can include information about his/her fatigue level which is received from the smart watch worn by the rescuer.

Other users may then access the data in the central server system 920. For example, as shown here, an emergency room physician 922 is operating his or her own tablet 924 that communicates wirelessly, such as over a cellular data network. As such, the physician 922 may review the data from central server system 920. In this manner, the system 900 permits various portable electronic devices to communicate with each other so as to coordinate care that is provided to a victim 902. In addition, the system 900 allows the technician 914 and others to see raw real-time data and derived real-time or historical data about a rescue attempt.

Many other implementations other than those described may be employed, and may be encompassed by the following claims.

What is claimed is:

1. A medical system for assisting one or more rescuers in providing resuscitative care, the medical system comprising:
   a chest compression sensor including one or more accelerometers configured to:
   sense chest compression motion associated with cardiopulmonary resuscitation (CPR) chest compressions performed by a rescuer, and
   generate one or more signals indicative of the chest compression motion;
   a wrist-worn device physically separate from the chest compression sensor, the wrist-worn device comprising one or more output devices and one or more physiological sensors to generate one or more signals indicative of at least one physical parameter of the rescuer;
   a defibrillator comprising at least one processor communicatively coupled to the chest compression sensor and the wrist-worn device, the at least one processor configured to:
   receive, from the chest compression sensor, the one or more signals indicative of the chest compression motion,
   analyze the one or more signals indicative of the chest compression motion to determine at least one chest compression parameter and generate chest compression feedback based on the at least one chest compression parameter,
   transmit the chest compression feedback to the wrist-worn device and cause the wrist-worn device to provide the chest compression feedback via the one or more output devices,
   determine if the rescuer is currently administering chest compressions to the patient, and
   transmit a signal to the wrist-worn device to display feedback data via the one or more output devices based on the determination of whether or not the rescuer is currently administering chest compressions to the patient, wherein the displayed feedback data corresponds to chest compression feedback when the rescuer is performing chest compressions or other feedback if the rescuer is not performing chest compressions.

2. The system of claim 1, wherein the wrist-worn device includes a band formed of multiple spring like metal bands that, upon an application of pressure, wrap around the wrist, securing the wrist-worn device to the rescuer.

3. The system of claim 1, wherein the at least one chest compression parameter includes at least one of a depth of chest compressions and a rate of chest compressions.

4. The system of claim 3, wherein the one or more output devices of the wrist-worn device includes a visual display configured to display the at least one chest compression parameter to the rescuer.

5. The system of claim 1, wherein the wrist-worn device further comprises a memory configured to store a unique identifier associated with the wrist-worn device.

6. The system of claim 1, wherein the wrist-worn device is configured to turn on when the wrist-worn device wraps around the wrist.

7. The system of claim 1, wherein the one or more physiological sensors of the wrist-worn device include at least one of a blood pressure sensor, an ECG sensor, a heart rate sensor, a pulse oximetry sensor, and a colorimeter.

8. The system of claim 1, wherein the chest compression sensor includes a puck housing the one or more accelerometers, the puck being electrically coupled to the defibrillator.

9. The system of claim 1, wherein the wrist-worn device includes one or more additional accelerometers.

10. The system of claim 1, wherein the at least one processor of the defibrillator is configured to determine an incomplete release of the chest during CPR chest compressions based on the one or more signals indicative of the chest compression motion.

11. The system of claim 1, wherein the wrist-worn device provides a communications network node in a communications network comprising a plurality of wearable computing devices corresponding to a plurality of emergency response team members.

12. The system of claim 1, wherein the defibrillator is configured to transmit information to a central management system.

13. The system of claim 1, wherein the wrist-worn device is configured to receive patient information from the defibrillator.

14. The system of claim 13, wherein the patient information includes one or more of heart rate information, blood pressure information, inspired carbon dioxide information, and ECG information.

15. The system of claim 1, wherein the chest compression feedback provided by the one or more output devices of the wrist-worn device is at least one of haptic feedback, audible feedback, and visual feedback.

16. The system of claim 15, wherein the wrist-worn device is configured to provide the haptic feedback at specific intervals to indicate when the rescuer should be performing the CPR chest compressions.

17. The system of claim 1, wherein the at least one processor is further configured to transmit a signal to the wrist-worn device to provide ventilation feedback to the rescuer.

18. The system of claim 1, wherein the at least one processor of the defibrillator transmits a signal to the wrist-worn device using a wireless protocol.

19. The system of claim 18, wherein the wireless protocol includes at least one of a Bluetooth 4 protocol and a wireless protocol.

20. The system of claim 1, wherein the feedback data includes a visual indicator to switch tasks.

21. The system of claim 20, wherein the visual indicator to switch tasks includes cycling arrows displayed on the one or more output devices of the wrist-worn device.

22. The system of claim 1, wherein the other feedback comprises at least one of ventilation feedback or patient data.

23. A method for assisting one or more rescuers in providing resuscitative care, the method comprising:
generating, by one or more accelerometers disposed within a chest compression sensor and configured to sense motion associated with cardiopulmonary resuscitation (CPR) chest compressions performed by a rescuer, one or more signals indicative of chest compression motion;
receiving, by a defibrillator, the one or more signals indicative of the chest compression motion;
receiving, by the defibrillator, one or more signals indicative of at least one physical parameter of the rescuer from one or more physiological sensors of a wrist-worn device worn by the rescuer and physically separate from the chest compression sensor;
analyzing the one or more signals to determine at least one chest compression parameter;
generating chest compression feedback based on the at least one chest compression parameter;
transmitting the one or more signals indicative of the chest compression parameter to the wrist-worn device to cause the wrist-worn device to output chest compression feedback to one or more output devices of the wrist-worn device;
determining if the rescuer is currently administering chest compressions to the patient, and
transmitting a signal to the wrist-worn device to display feedback data via the one or more output devices based on the determination of whether or not the rescuer is currently administering chest compressions to the patient, wherein the displayed feedback data indicates that the rescuer switch tasks, and wherein the displayed feedback data corresponds to chest compression feedback when the rescuer is performing chest compressions or other feedback if the rescuer is not performing chest compressions.

24. The method of claim 23, comprising: sensing, by one or more physiological sensors on the wrist-worn device, one or more physical parameters of the rescuer.

25. The method of claim 24, wherein the one or more physical parameters comprise at least one of a heart rate and a blood pressure of the rescuer.

26. The method of claim 23, wherein the at least one chest compression parameter, includes one or more of a depth of chest compressions and a rate of chest compressions.

27. The method of claim 26, comprising displaying, by the wrist-worn device, feedback indicative of the depth of chest compressions and the rate of chest compressions.

28. The method of claim 23, comprising:
determining an incomplete release of the chest during CPR chest compressions based on the one or more signals indicative of the chest compression motion.

29. The method of claim 23, comprising transmitting, by the defibrillator, information to a central management system.

30. The method of claim 23, comprising receiving, at the wrist-worn device, patient information from the defibrillator.

31. The method of claim 30, wherein the patient information includes one or more of heart rate information, blood pressure information, inspired carbon dioxide information, and ECG information.

32. The method of claim 23, wherein the one or more physiological sensors of the wrist-worn device include at least one of a blood pressure sensor, an ECG sensor, a heart rate sensor, a pulse oximetry sensor, and a colorimeter.

33. The method of claim 23, wherein the other feedback comprises at least one of ventilation feedback or patient data.

* * * * *